United States Patent [19]

Warren, III et al.

[11] Patent Number: 4,828,978
[45] Date of Patent: May 9, 1989

[54] AGGLUTINATION REAGENT AND METHOD OF PREPARING SAME

[75] Inventors: Harold C. Warren, III, Rush; Brian A. Snyder, Rochester, both of N.Y.

[73] Assignee: Eastman Kodak Company, Rochester, N.Y.

[21] Appl. No.: 98,432

[22] Filed: Sep. 18, 1987

[51] Int. Cl.⁴ ............... G01N 33/547; G01N 33/569; G01N 33/571
[52] U.S. Cl. ........................................... 435/5; 435/7; 435/36; 436/511; 436/533; 436/547; 436/818
[58] Field of Search ............... 436/533, 534, 511, 818, 436/547; 435/5, 7, 36

[56] References Cited

U.S. PATENT DOCUMENTS

| | | | |
|---|---|---|---|
| 4,590,156 | 5/1986 | Dorsett | 436/533 X |
| 4,591,571 | 5/1986 | Kuboyama et al. | 436/533 |
| 4,690,906 | 9/1987 | Duheille | 436/533 X |
| 4,690,908 | 9/1987 | Mochida | 436/533 X |

FOREIGN PATENT DOCUMENTS 124320 11/1984 European Pat. Off. .
50-82229 7/1975 Japan .

OTHER PUBLICATIONS

Maggio(ed), *Enzyme-Immunoassay*, CRC Press, Inc., Boca Raton, Fla., 1980, pp. 71-75.
Kaplan et al., *Biochim. Biophys. Acta*, 728 (1983), pp. 112-120.

*Primary Examiner*—Sidney Marantz
*Attorney, Agent, or Firm*—J. Lanny Tucker

[57] ABSTRACT

An agglutination reagent is prepared by covalently attaching an immunoreactive species to polymeric particles through reactive groups in the species. After attachment, the species is chemically modified with an acylating, alkylating or sulfonylating agent thereby modifying primary or secondary amino groups. The reagent can be used in agglutination assays for a number of analytes, including Streptococcus A antigen, human retroviruses or antibodies, human chorionic gonadotropin and other antibodies or antigens.

19 Claims, 1 Drawing Sheet

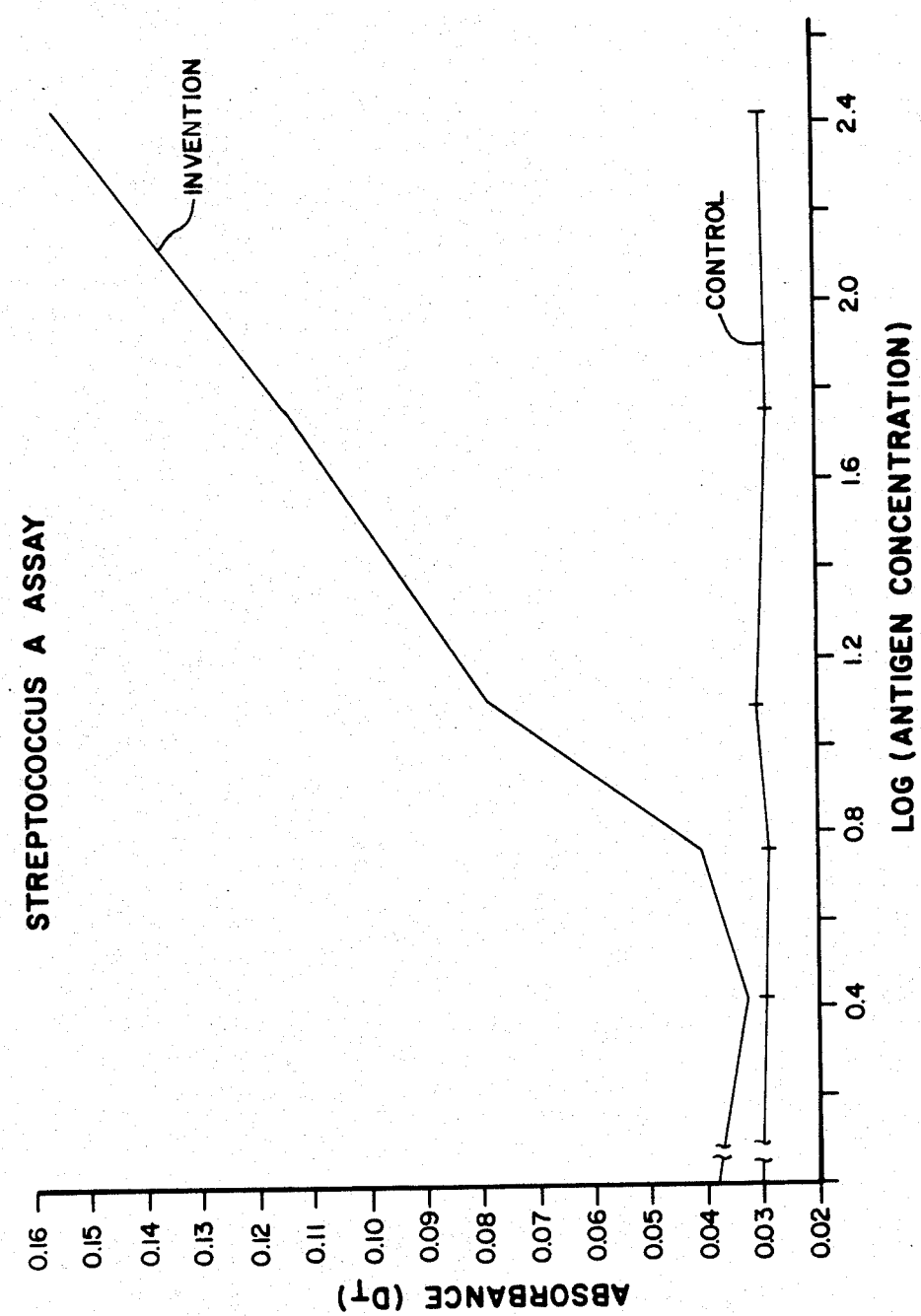

AGGLUTINATION REAGENT AND METHOD OF PREPARING SAME

FIELD OF THE INVENTION

This invention relates to an agglutination reagent and a method of preparing it. This reagent is useful in immunoassays and diagnostic analytical procedures.

BACKGROUND OF THE INVENTION

The antigen-antibody reaction is the basis for all immunological test methods. Certain proteins known as antibodies are produced by mammals in response to the presence of an antigen, that is a foreign substance, which can be another protein or a carbohydrate. This normal body response to a foreign substance has led to the development of a number of techniques which are used to diagnose various diseases, disorders and physiological conditions. In a general sense, one component of an antibody-antigen reaction can be defined as the immunoreactive species while the corresponding component which complexes with it is considered the receptor.

In vitro tests for the presence of a suspected protein, antigen or antibody in a biological sample are carried out by adding the immunological counterpart to the biological sample. If the suspected substance is present, the resulting antigen-antibody reaction can be demonstrated by precipitation of the antigen-antibody complex. This reaction complex is generally difficult to detect visually. For this reason, either antibodies or antigens are often bound to insoluble particles, for example polymer latex particles, so that when the complex is formed, it is readily detectable from the resulting agglutination either by observing the presence of clumping or by a detectable tracer associated with the particles. Agglutination then is characterized by the clumping of particles from a suspension of particles. Further details of known agglutination methods are provided in U.S. Pat. Nos. 4,419,453 (issued Dec. 6, 1983 to Dorman et al) and 4,459,361 (issued July 10, 1984 to Gefter).

Biological samples which are assayed for various analytes may contain materials which cause nonspecific interactions of the immunoreactive species and the corresponding receptor. These nonspecific interactions may undesirably influence the assay results by showing false positives or by providing a high background so that a true positive result is difficult to detect. In addition, the polymeric particles to which immunoreactive species or receptors are attached can interact with each other due to surface charges. Moreover, the species or receptors attached to the particles can interact with each other as well, causing unwanted agglutination and inaccurate results.

Various methods have been devised to reduce nonspecific interactions, including controlling the assay pH and adding materials to modify attached proteins. One such method is described in U.S. Pat. No. 4,591,571 (issued May 27, 1986 to Kuboyama et al). This reference describes an agglutination reagent having antibodies absorbed to carrier particles. Prior to attachment, the antibodies are chemically modified with an acylating agent. It is alleged that such treatment reduces nonspecific interactions.

When an immunoreactive species was prepared using the teaching of U.S. Pat. No. 4,591,571, that is, modifying the antibodies by succinylation before attachment to beads, no signal was obtained (see Example 6 below).

SUMMARY OF THE INVENTION

The problems noted above with the prior art reagents and methods are overcome with a method for preparing an agglutination reagent comprising:

A. covalently attaching an immunoreactive species to polymeric particles having a tracer material associated therewith, and B. chemically modifying the attached immunoreactive species with an acylating, alkylating or sulfonylating agent.

This invention also provides an agglutination reagent comprising an immunoreactive species covalently attached to polymeric particles having a tracer material associated therewith, the attached immunoreactive species having free primary and secondary amino groups modified with an acylating, alkylating or sulfonylating agent.

The present invention provides an agglutination reagent which exhibits reduced nonspecific interactions, and which is highly sensitive to the analyte of interest. These advantages are achieved by first covalently attaching an immunoreactive species, which is a receptor for the analyte of interest, to polymeric particles, followed by chemical modification with an acylating, alkylating or sulfonylating agent to chemically modify primary and secondary amine groups. This is directly contrary to the teaching of U.S. Pat. No. 4,591,571, noted above. It is shown in Example 6 below that a reagent prepared using the teaching of that patent is ineffective in a diagnostic assay whereas the reagent of the present invention is very useful in such an assay.

BRIEF DESCRIPTION OF THE DRAWING

The FIGURE shows graphical plots of absorbance versus Streptococcus A antigen concentration for a reagent of the present invention as compared to a Control reagent prepared according to U.S. Pat. No. 4,591,571, noted above. This comparison is described in detail in Example 6 below.

DETAILED DESCRIPTION OF THE INVENTION

The present invention provides an agglutination reagent useful in a diagnostic test for an immunoreactive species (mono- or multivalent) which can be performed in a very short time, that is less than about 10 minutes, and without the use of complicated equipment. This permits the test to be performed in a doctor's office or at home and enables the doctor or home user to know the results of the test very quickly. The test detects the presence of the species in a biological sample, such as a swab specimen from the throat, urine specimen or sample of another aqueous liquid. Such biological samples can be tested with or without pretreatment (for example, filtration) to remove unwanted debris or interferents.

The reagent of this invention can be used to detect and quantify any of a wide variety of immunoreactive species. For purposes of definition, the immunoreactive species to be determined is defined as a ligand herein. Such ligands are generally proteins, drugs, steroids, glycoproteins, glycolipids, carbohydrates or other biological or chemical compounds of interest which have one or more sites for complexing with a corresponding receptor, for example, corresponding antibodies for antigens. Alternatively, the ligand can be an antibody which has one or more complexing sites reactive with the corresponding antigen or an anti-antibody. Ligands which can be detected with the reagent of this invention include, but are not limited to, Streptococcus A antigen, antigens from chlamydial and gonococcal organisms, antigens from retroviruses such as HTLV and HIV (human immunodeficiency virus) or antibodies directed against such, human chorionic gonadotropin (hCG), leutinizing hormone (LH), herpes viruses, drugs, antibiotics, and other hormonal, bacterial or viral antigens and antibodies. In some instances, the ligand must be extracted from the organism or virus found in the biological specimen. In other instances, the ligand is already in a reactive form and requires no extraction procedures prior to the assay. Extraction procedures for a given ligand are known to one skilled in the art. Exemplary extraction procedures for Streptococcus A antigen are described below. In still other instances, the ligand can be detected as part of an organism or virus without any extraction step.

Preferably, the reagent is used to detect Streptococcus A antigen as is demonstrated in the following embodiment and in Example 1 below. This embodiment relating to Streptococcus A antigen is presented for illustrative purposes, but it will be understood that the scope of this invention is not so limited. A biological sample suspected of containing the antigen can be collected from a patient in any suitable manner. Subsequently, if necessary, the antigens are extracted from the organisms in a suitable manner. A preferred extraction procedure includes dipping the swab in a suitable extraction composition containing one or more reagents which singly or in combination cause release of the Streptococcus A antigen from the organism, specimen cells and other debris in the sample.

Useful extraction compositions known in the art for Streptococcus A antigen include a mixture of nitrite salt and glacial acetic acid, as described in E.P. Publication 150,567, and enzymes derived from the bacterium *Streptomyces albus* as described in U.S. Pat. No. 4,618,576 (issued Oct. 21, 1986 to Rosenstein et al). A preferred extraction composition is a mixture of a nitrite salt (for example, sodium nitrite or potassium nitrite) with an organic acid (for example, succinic, malonic or citric acid), as described in copending and commonly assigned U.S.Ser. No. 098,431, filed on even date herewith by Snyder et al and entitled KIT FOR EXTRACTING STREPTOCOCCUS A ANTIGEN AND A METHOD OF USING EXTRACTED ANTIGEN, now abandoned in favor of Continuation-in-Part U.S. application Ser. No. 131,618 filed Dec. 11, 1987.

The presence of a ligand, for example Streptococcus A antigen, is detected using the agglutination reagent of this invention which comprises water-insoluble carrier particles having another immunoreactive species (which is a receptor for the ligand) covalently bound to the particles. Reaction (or immunochemical binding) between the ligand and receptor then results in a linking together of the particles so that they agglutinate and precipitate out of suspension. This agglutinate can be suitably detected using tracer materials associated with the particles.

Suitable particles useful in the reagent can be natural or synthetic particles which are water-insoluble and capable of having an immunoreactive species covalently bound thereto in a suitable manner. Examples of useful carrier particles include ferritin crystals, agarose particles, glass beads, polymeric particles, such as latex particles, and others known in the art which have reactive groups on the particle surface for covalent reaction with immunoreactive species. The following references describe representative useful particles: U.S. Pat. Nos. 3,700,609 (issued Oct. 24, 1972 to Tregear et al), 3,853,987 (issued Dec. 10, 1974 to Dreyer), 4,108,972 (issued Aug. 22, 1978 to Dreyer), 4,401,765 (issued Aug. 30, 1983 to Craig et al), 4,419,453 (issued Dec. 6, 1983 to Dorman et al), 4,459,361 (noted above), 4,478,946 (issued Oct. 23, 1984 to Van der Merwe) and 4,591,571 (noted above). The particles useful in this invention are generally quite small, that is less than about 2 micrometer in diameter. Preferably, they have an average diameter of from about 0.1 to about 1 micrometer.

The particles must have groups on the outer surfaces which can form covalent bonds with the immunoreactive species. Such groups include, but are not limited to, carboxyl, amine, epoxy, aldehyde, haloalkyl, activated 2-substituted ethylsulfonyl, vinylsulfonyl, vinylsulfonylalkylene and others known in the art. These groups can be incorporated into the particles in any suitable manner, for example, during manufacture, or just prior to attachment of the immunoreactive species. The haloalkyl, activated 2-substituted ethylsulfonyl, vinylsulfonyl and vinylsulfonylalkylene groups are preferred.

Particularly useful carrier particles are polymeric latex particles, and more preferably they are what are known in the art as core-shell polymeric latex particles. A wide variety of monomers can be used in the preparation of such particles as long as the particles are water-insoluble. A worker skilled in the polymer chemistry art would be able to design and prepare suitable latex particles. Preferred core-shell polymeric latex particles in the practice of this invention are described in Examples 1 and 3 below. These particles have a core composed of homo- or copolymers of styrene, or other monomers which have high affinity for a tracer material (described below) and a shell composed of homo- or copolymers which have the desired reactive groups free for reaction with the immunoreactive species.

The particles useful in the practice of this invention have sufficient tracer molecules associated therewith in order to allow quantitative determination of the ligand from the amount of tracer seen in either the agglutinate or in the unagglutinated residual materials. The tracer molecules can be suitably attached to the outer surface of the particles, or more preferably, distributed within the particles. Any tracer material which allows detection of the agglutinate can be used. If ferritin crystals are used as the particles, the tracer molecules are molecules of iron inherently in those crystals. Other natural or synthetic particles can have, as tracers: radioisotopes, colorimetric compounds, fluorescent compounds, bioluminescent compounds, chemiluminescent compounds, phosphorescent compounds and other detectable materials known in the art. Preferably, the tracer is a radioisotope, colorimetric compound or fluorescent compound (for example, a dye or rare earth chelate). A worker skilled in the art would be able to combine an appropriate tracer with the particular particle used.

In one embodiment, the tracer can be a fluorescent rare earth chelate such as an europium chelate, as described for example, U.S. Pat. No. 4,259,313 (issued Mar. 31, 1981 to Frank et al). In another and preferred embodiment, the tracer is a colorimetric compound which is readily detected in the agglutinate. Useful dyes are known in the art. Some dyes can be incorporated into the particles when the particles are prepared. Alternatively, the dyes are imbibed into preformed particles in such a manner that they do not leach out.

The tracer can be distributed within the particles in any suitable manner. For example, the tracer can be uniformly distributed therein as shown for example in U.S. Pat. No. 3,843,987 (noted above). Preferably, the tracer molecules are located in a restricted area of the particles, for example, near the surface or predominately in the interior thereof. In the preferred core-shell particles, the tracer can be in either the core or shell, but most preferably, substantially all of it is in the core of the particles.

An immunoreactive species (that is, a receptor molecule reactive with the ligand) is covalently attached to the outer surfaces of the particles in a suitable manner using known procedures and reagents if needed. When the attached species is an antibody, either monoclonal or polyclonal antibodies can be used. Antibodies can be obtained commercially or prepared using known techniques. Either whole antibodies or fragments thereof may be used.

The attached immunoreactive species can be an antigen if the ligand is an antibody. One such reagent is an agglutination reagent useful for detecting antibodies to a human retrovirus antigen, for example, antibodies to HTLV-I or HIV-I antigen.

After attachment, the immunoreactive species is chemically modified with a suitable modifying agent which is capable of modifying primary and secondary amine groups. Examples of such modifying agents include acylating agents, alkylating and sulfonylating agents, some of which are described, for example, in *Enzyme-Immunoassay*, Maggio (Ed.), CRC Press, Inc., Boco Raton, Fla., 1980, pp. 72-77.

Representative useful acylating agents are described in U.S. Pat. No. 4,591,571 (noted above). Preferred acylating agents are selected from the group consisting of anhydrides, acyl halides and esters derived from dicarboxylic and polycarboxylic acids (three or more acid groups). The anhydrides, such as succinic anhydride, are most preferred. Representative alkylating and sulfonylating agents, such as bromoacetic acid, chloroacetic acid, fluoronitrobenzene, bromomalonic acid, bromopropionic acid, m-(chlorosulfonyl)benzoic acid and p-(chlorosulfonyl)benzoic acid are also useful with bromoacetic acid being most preferred.

The chemical modification step of the method of this invention can be carried out generally by first covalently immobilizing the immunoreactive species onto the particles. Casein may also be immobilized thereon at the same time. The immobilized species is then modified with a suitable acylating, alkylating or sulfonylating agent under the appropriate conditions for a given agent. Such conditions are known to one skilled in the art. Representative procedures are described in Examples 1, 4 and 5 below.

In the modification process, the number of free primary and secondary amino groups of the immobilized immunoreactive species which are modified will depend upon the pH of the medium, the concentration of reagents and immunoreactive species. But a sufficient modification can be achieved by one skilled in the art using the teaching provided herein. Generally, the amount of modifying agent used is 10% of the amount of species present by weight.

Once an agglutinate has been formed in an assay, agglutinated materials are separated from unagglutinated materials in any suitable manner known in the art. Generally, the separation is accomplished with a filtration technique. Following separation, the amount of either the agglutinated or unagglutinated materials is determined using known procedures.

While the present invention is not so limited, the assay for ligand can be carried out using a suitable test device which comprises a microporous membrane. Such a device can have one or more wells to which a specimen containing the ligand is added for reaction with the species on the surface of the agglutination reagent. The reagent can be added to the device during the assay, or incorporated therein at the time of manufacture. Once the agglutinate is formed, the unagglutinated residual materials can be washed through the membrane with the wash solution into a separate compartment below the membrane. An example of such a test device is described and claimed in copending and commonly assigned U.S.Ser. No. 19,810 filed Feb. 27, 1987 by Hinckley. Other variations of useful test devices would be within the purview of an ordinary worker skilled in the art.

In the examples which follow, illustrating the practice of this invention, the materials used were obtained as follows:

nylon 66 membranes from Pall Corp. (Glen Cove, N.Y.),

Oil Red EGN dye from Aldrich Chemical Co. (Milwaukee, Wis.), monoclonal antibodies to the PI antigen of serogroup B of *Neisseria gonorrhea* were obtained using the F62 strain according to the procedure described by Schneider et al in *J. Immun. Meth.*, 54, pp. 10–105, 1982, monoclonal antibodies to Streptococcus A antigen were obtained from a Streptococcus A vaccine according to the procedure described by McCarty et al, *J. Exp. Med.*, 102, 11, 1955, monoclonal antibodies to hCG were mouse $IgG_1$ antibodies produced by standard hybridoma technology and had affinities of about $10^9$ molar$^{-1}$, casein, human chorionic gonadotropin and bovine serum albumin from Sigma Chemical Co. (St. Louis, Mo.), and the remainder either from Eastman Kodak Co. (Rochester, N.Y.) or prepared using standard starting materials and procedures.

EXAMPLE 1

PREPARATION AND USE OF AN AGGLUTINATION REAGENT FOR STREPTOCOCCUS A DETERMINATION

This example demonstrates the preparation of an agglutination reagent of this invention and its use to determine Streptococcus A antigen.

Core-shell polymeric latex particles containing a red dye (Oil Red EGN) in the core were prepared by imbibing the dye into the particles that had been prepared using core/shell polymerization techniques. Dye was incorporated using the techniques described in Belgian Pat. No. 843,647 (published Dec. 30, 1976). The core of the particles was composed of poly(styrene-co-2-acetoacetoxyethyl methacrylate) (70:30 weight ratio) while the shell was composed of poly(m,p-chloromethylstyrene). The average diameter of the particles was about 0.45 micrometer. Monoclonal antibodies to Streptococcus A antigen and casein were covalently immobilized on these particles as follows: to 0.6 ml of 50 mmolar borate buffer (pH 8.5) was added 0.1 mg of total protein comprised of a 10:1 mixture of anti-Strep A antibody (2.9 mg/ml solution in phosphate buffered saline solution, known in the art as PBS) and casein (10 mg/ml water). After mixing, 41.5 $\mu$l of a 5% suspension of the polymeric latex particles were added (to provide 0.3% solids) and the resulting solution was rotated (end-over-end) for 24 hours at 37° C. to effect covalent attachment of the antibody and the casein to the particles to form an agglutination reagent.

A solution of succinic anhydride (10 mg/ml dimethyl sulfoxide) was added to a suspension of the agglutination reagent described above at a weight ratio of 1 part anhydride to 1 part total protein. The resulting suspension was mixed for four hours at 25° C., then centrifuged for 5 minutes at 7000 rpm and the resulting pellet was resuspended in 0.1 molar glycine buffer (pH 8.5) to a concentration of 0.3% solids. This procedure chemically modified the primary and secondary amine groups of the proteins attached to the particles.

Streptococcus A antigen was extracted from an isolate obtained from a local hospital at 25° C. for 1 minute using a solution of equal volumes or sodium nitrite (8 molar) and citric acid (0.2 molar). The solution was then neutralized with an equal volume of 3-(N-morpholino)-propanesulfonic acid buffer (2 molar, pH 7.5) containing ethylenediaminetetraacetic acid (75 mmolar).

A nylon 66 microporous membrane (5 $\mu$m average pore size) was incorporated into a test well of a disposable test device like that described and claimed in U.S.Ser. No. 19810 of Hinckley, noted above, and pretreated by washing with 100 $\mu$l of a 2% succinylated casein solution.

A mixture of sodium chloride (80 $\mu$l, 1 molar), the agglutination reagent suspension described above (40 $\mu$l), and extracted antigen (80 $\mu$l) containing about 4.2 x $10^5$ colony-forming units was added to the test well of the test device containing the membrane, and incubated therein for two minutes at 25° C. The fluid was then allowed to drain into a compartment below the membrane, and the agglutinate on the membrane was washed with 150 $\mu$l of a wash fluid having an ionic strength of 0.25.

After the washing step, the amount of dye in the agglutinate on the membrane was measured at 540 nm using reflectance measuring equipment. The Williams-Clapper transform (*J. Optical Soc. Am.*, 43, p. 595, 1953) was used to calculate transmission density values. The agglutinate on the membrane was readily observable and had a significantly greater density value than the density of a background control (the difference was 0.148). These data indicate that the agglutination reagent of the present invention was useful for determination of Streptococcus A antigen from a biological sample.

EXAMPLE 2

DETERMINATION OF GONORRHEA

This example demonstrates the use of the agglutination reagent of the present invention for the determination of gonorrhea. The agglutination reagent used in this example was composed of latex particles comprised of poly(styrene-co-m,p-chloromethylstyrene-co-2-hydroxyethyl acrylate) (76:23:1 weight ratio) into which had been imbibed 5%, by weight of europium (III) (thenoyltrifluoroacetone)$_3$ along with trioctylphosphine oxide on the ratio of 1 part chelate to 2 parts oxide according to the procedures described in Belgian Pat. No. 843,647. The particles had an average diameter of about 0.45 micrometer.

Monoclonal antibodies to the PI antigen of the serogroup B of *Neisseria gonorrhea* (also known in the art as the PIB antigen) were covalently immobilized on the particles described above as follows: to 1.3 ml of 50 mmolar borate buffer (pH 8.5) was added 0.15 ml of 1.08 mg/ml antibody solution in phosphate buffered saline (PBS). In addition, 0.32 ml of a 1 mg/ml aqueous solution of casein was added in order to immobilize casein on the particles as well.

After mixing, 41.5 $\mu$l of a 5% suspension of the latex particles described above were added, and the resulting solution was mixed at 37° C. for 24 hours. Succinic anhydride (0.174 ml of 10 mg/ml dimethyl sulfoxide solution) was added, and the resulting solution was mixed at 22° C. for four hours in order to modify the amine groups of the attached proteins. This solution was then centrifuged for 10 minutes and the resulting pellet was resuspended in 0.1 molar glycine (pH 8.5) to give a mixture containing 0.3% solids of agglutination reagent.

The PIB antigen was extracted from a specimen of *Neisseria gonorrhea* using a mixture of 1% ethanolamine and 10 mmolar ethylenediaminetetraacetic acid, followed by sonication and filtration.

A nylon 66 microporous membrane having an average pore size of 5 micrometers was pretreated by dipping it into a 2% casein solution. A mixture of sodium chloride (50 $\mu$l, 6 molar), antigen solution (50 $\mu$l) having a specific amount of antigen (nanogram) and the agglutination indicator solution described above (50 $\mu$l) was added to a test tube, incubated at 22° C. for 30 minutes, then filtered through the treated microporous membrane. The resulting agglutinate on the membrane was washed with 0.15 $\mu$l of 1 molar tricine buffer (pH 8.6). The amount of agglutinate was determined by measuring the amount of fluorescence in the agglutinate using standard surface fluorescence measuring equipment (excitation, 342 nm and emission, 610 nm). A Control solution containing specific amounts of an extract of a different antigen (that is, the PI antigen of the serogroup A of *Neisseria gonorrhea*, or also known as the PIA antigen) was treated in the same manner in order to measure nonspecific interactions with the antibodies to the PIB antigen. Table I below shows the results of these tests. It is clear that the assay of this invention can be used to determine a desired antigen of a specific serogroup of gonorrhea.

TABLE I

| PIB Antigen Concentration (ng) | Relative Fluorescence | |
|---|---|---|
| | Test | Control |
| 100 | 107 | 32 |
| 10 | 332 | 120 |
| 1 | 248 | 73 |

EXAMPLE 3

ASSAY FOR HUMAN CHORIONIC GONADOTROPIN

This example demonstrates the practice of the present invention for the determination of human chorionic gonadotropin (hCG).

Core/shell polymeric particles were imbibed with Oil Red EGN dye according to known procedures. The particle cores were composed of poly(styrene-co-2-acetoacetoxyethyl methacrylate) (85:15 weight ratio), and the particle shells were composed of poly(m,p-chloromethylstyrene-co-methacrylic acid) (99.8:0.2 weight ratio). The particles had an average diameter of about 0.32 micrometer.

Monoclonal antibodies to two different epitopic sites of hCG and casein were covalently immobilized on these particles as follows: to 0.6 ml of 50 mmolar borate buffer (pH 8.5) were added 0.1 mg of 10:1 mixture of hCG antibody (2.9 mg/ml phosphate buffered saline solution) and casein (10 mg/ml water). After mixing, 41.5 µl of a 5% suspension of the latex particles described above were added and the resulting suspension was rotated (end-over-end) for 24 hours at 37° C. to effect covalent attachment of the antibodies and casein to the particles to form an agglutination reagent.

A solution of succinic anhydride (10 mg/ml dimethyl sulfoxide) was added to a mixture of the agglutination reagent at a weight ratio of 1 part anhydride to 1 part total protein, and the resulting mixture was mixed for 4 hours at 25° C., centrifuged for 5 minutes at 7000 rpm in order to chemically modify the amine groups of the attached proteins. The resulting pellet was resuspended in 0.1 molar glycine (pH 8.5) to a concentration of 0.3% solids.

Various amounts of hCG (milli I.U./ml) were added to phosphate buffered saline solutions (0.1 molar sodium phosphate and 0.15 sodium chloride) containing 0.5% bovine serum albumin. A nylon 66 microporous membrane having an average pore size of about 5 micrometers was incorporated into a test well of a disposable test device similar to that described in Example 1 above. This membrane was washed with 2 drops of a 1% aqueous solution of succinylated casein. The hCG concentration in milli I.U. is defined as 5000 milli I.U. being equivalent to 1 microgram of purified hCG.

A mixture of 60 µl of 4 molar sodium chloride, 1 molar tricine buffer (pH 8.6), 60 µl of suspension of the agglutination reagent described above and 240 µl of the hCG solutions described above was added to test tubes, gently mixed and allowed to incubate at 25° C. for 10 minutes. A portion of each solution (300 µl) was added to the test well containing the membrane and allowed to flow through the membrane. Agglutinate formed on the membrane did not flow through, however. It was washed with 300 µl of a 1 molar sodium chloride solution, and the amount of dye in the agglutinate was measured at 540 nm as described in Example 1. The results of these measurements are shown in Table 11 below as transmission density ($D_T$). It indicates that the assay of this invention can be used to determine hCG.

TABLE II

| hCG Antigen (milli I.U./ml) | $D_T$ |
|---|---|
| 0 | 0.043 |
| 500 | 0.047 |
| 1000 | 0.133 |

EXAMPLE 4

PREPARATION OF AGGLUTINATION REAGENTS USING ALKYLATING REAGENTS

This example illustrates the modification of immobilized antibodies using three different alkylation reagents: chloroacetic acid, bromoacetic acid and bromopropionic acid, to prepare reagents of this invention.

Core-shell polymeric latex beads, comprising a core of poly(styrene-co-acetoacetoxyethyl methacrylate) (70:30 molar ratio) and a shell of poly-(m&p-chloromethylstyrene), were prepared and imbibed with a 2.5% acetonitrile solution of Oil Red EGN dye using the procedure described in Example 1. The dyed beads were suspended in 0.05 molar sodium borate buffer (pH 8.5) containing 0.1% sodium azide to provide a suspension of 0.3% solids.

Monoclonal antibodies to Strep A antigen and casein were immobilized onto the beads as described in Example 1.

The immobilized antibody mixture (0.012 ml) was mixed with the appropriate alkylating reagent (0.012 ml of a 10 mg/ml dimethylsulfoxide solution) and heated at 37° C. for 18 hours, then centrifuged at 7000 rpm for 5 minutes. The resulting pellet was suspended in 0.1 molar glycine buffer (pH 8.5) to provide the agglutination reagent as a 0.3% solid suspension.

EXAMPLE 5:

AGGLUTINATION REAGENT USING POLYMER DERIVED FROM A CHLOROMETHYLSULFONYL MONOMER

Core-shell polymeric latex beads, comprising a core of poly(styrene-co-acetoacetoxyethyl methacrylate) (85:15 molar ratio) and a shell of poly-[styrene-co-m & p-(2-chloroethylsulfonylemthyl)-styrene](95.5:4.5 molar ratio), were prepared and imbibed with a 3.5% acetonitrile solution of Oil Red EGN dye as described in Example 1. The beads were suspended in 0.05 molar sodium borate buffer (pH 8.5) containing 0.1% sodium azide to provide a 0.3% solid suspension.

Monoclonal antibodies to Strep A [0.026 ml of a 3.8 mg/ml solution in 0.05 molar borate buffer (pH 8.5) containing 0.1% sodium azide]and casein (0.01 ml of a 1 mg/ml solution in water) were mixed together in about 0.9 ml of borate buffer.

The beads (0.173 ml of a 1.73% buffer suspension) were added, and the mixture was mixed end-over-end for 24 hours at about 25° C. Succinic anhydride (0.01 ml of a 10 mg/ml of dimethylsulfoxide solution) was added, and the mixture was rocked for 3 hours. The mixture was centrifuged, the supernatant decanted, and the pellet was suspended in 0.1 normal glycine (pH 8.5) containing 0.1% sodium azide to provide a 0.3% solid suspension.

EXAMPLE 6:

ASSAY FOR STREPTOCOCCUS A

This example shows an assay for Strep A comparing an agglutination reagent prepared by the method of the present invention to an agglutination reagent prepared by the method taught in U.S. Pat. No. 4,591,571 (noted above).

The agglutination reagent of the present invention was prepared and tested in a Strep A assay as follows:

Core-shell polymeric latex beads, comprising a core of poly(styrene-co-2-acetoacetoxyethyl methacrylate) (95:5 molar ratio) and a shell of poly-(m&p-chloromethylstyrene-co-methacrylic acid), (98:2 molar ratio) were prepared and imbibed with a 2% acetonitrile solution of Oil Red EGN dye according to Example 1.

The dyed beads were suspended in 0.05 molar sodium borate buffer (pH 8.5) containing 0.1% sodium azide to provide a suspension of 0.3% solids.

Monoclonal antibodies to Strep A antigen and casein were covalently immobilized onto these beads, and modified by treatment with succinic anhydride as described in Example 1.

Strep A antigen was extracted from an isolate obtained from a local hospital at 25° C. for one minute using a solution comprising 1.2 molar citric acid (10 μl) and 8 molar sodium nitrite (120 μl), then neutralized with 1 molar tricine, pH 8.5 (120 μl).

A nylon microporous membrane (5 μm Biodyne A from PALL Corporation) containing 1.07 g/m$^2$ of succinylated casein was incorporated into a disposable test device.

The bead composition (2 drops, about 90 μl) was added to the disposable, followed by 1 drop (about 40 μl) of the extracted antigen. After 2 minutes, the solution was allowed to drain through the membrane, then a wash solution of 1 molar sodium chloride (2 drops, about 90 μl) was added. The dye on the membrane was then read by reflectance, and the values were converted to transmission density ($D_T$). A plot of the data shown in FIG. 1, illustrates the improvement using our method.

A control agglutination reagent was prepared using the teachings of U.S. Pat. No. 4,591,371 to acylate the antibodies prior to immobilization. Attempts to covalently attach the modified antibodies to the particles were made using similar conditions described above. The resulting reagents were tested in a Strep A assay.

More specifically, for the Control reagent, monoclonal antibodies to Strep A antigen were first modified by treatment with succinic anhydride as follows: the antibodies (0.33 mg) were dissolved in 0.05 molar sodium borate buffer, pH 8.5 (0.9 ml), containing 0.1% sodium azide, and a solution of succinic anhydride (0.33 ml of a 10 mg/ml dimethylsulfoxide solution) was added. The mixture was then stirred for 3 hours at room temperature and then dialyzed against 0.05 molar borate buffer at 4° C. for about 16 hours.

The succinylated antibodies (0.5 ml of a 0.33 mg/ml borate buffer solution) and a solution of casein (0.0087 ml of a 1 mg/ml water solution) were mixed in 0.5 molar borate buffer, pH 8.5 (0.7 ml), containing 0.1% sodium azide. The dyed core-shell bead suspension (0.174 ml) was then added to the antibody/casein mixture and rotated end-over-end at 37° C. for 24 hours in an attempt to covalently attach the modified antibodies. The mixture was centrifuged, and the supernatant liquid decanted. The pellet was suspended in 0.1 molar glycine (pH 8.5) containing 0.1% sodium azide to provide a suspension of 0.3% solids.

A Control Strep A assay was run as described. A plot of the data is shown in FIG. 1. It is clear from the plotted data that very little agglutination was observed with the Control reagent. Apparently, modification of the antibodies prior to attachment does not allow a significant amount of covalent attachment of the antibodies.

The invention has been described in detail with particular reference to preferred embodiments thereof, but it will be understood that variations and modifications can be effected within the spirit and scope of the invention.

We claim:

1. A method for preparing an agglutination reagent comprising:
    A. covalently attaching an immunoreactive species to polymeric particles having a tracer material associated therewith, and
    B. chemically modifying said attached immunoreactive species with an acylating, alkylating or sulfonylating agent.

2. The method of claim 1 wherein said attached immunoreactive species is modified with an acylating agent.

3. The method of claim 2 wherein said acylating agent is selected from the group consisting of anhydrides, acyl halides and esters derived from dicarboxylic and polycarboxylic acids.

4. The method of claim 3 wherein said acylating agent is succinic anhydride.

5. The method of claim 1 wherein said immunoreactive species is an antibody.

6. The method of claim 5 wherein said immunoreactive species is an antibody against Streptococcus A antigen, human chorionic gonadotropin, a chlamydial antigen, a gonococcal antigen, a herpes virus or a human retrovirus.

7. The method of claim 1 wherein said immunoreactive species is an antigen.

8. A method for preparing an agglutination reagent for the determination of Streptococcus A antigen comprising:
    A. covalently attaching an antibody against Streptococcus A antigen to polymeric particles having a tracer material associated therewith, and
    B. chemically modifying said attached antibody with an acylating, alkylating or sulfonylating agent.

9. The method of claim 8 wherein said antibody is attached to said particles through reactive haloalkyl activated 2-substituted ethylsulfonyl, vinylsulfonyl or vinylsulfonylalkylene groups on the outer surface of said particles.

10. The method of claim 1 wherein said tracer molecules are distributed entirely within said particles.

11. The method of claim 1 wherein said particles are core/shell particles.

12. An agglutination reagent comprising an immunoreactive species covalently attached to polymeric particles having a tracer material associated therewith, said attached immunoreactive species having free primary and secondary amino groups modified with an acylating, alkylating or sulfonylating agent.

13. The reagent of claim 12 wherein said free amino groups have been modified with an acylating agent.

14. The reagent of claim 12 wherein said polymeric particles are core-shell particles having a tracer material in the core only.

15. The reagent of claim 14 wherein said tracer material is a dye.

16. The reagent of claim 12 wherein said immunoreactive species is an antibody.

17. The reagent of claim 12 wherein said immunoreactive species is an antibody to hCG.

18. The reagent of claim 12 wherein said immunoreactive species is a human retroviral antigen.

19. An agglutination reagent comprising antibodies to Streptococcus A antigen covalently attached to polymeric particles having a tracer material associated therewith, said attached antibodies having free primary and secondary amino groups modified with an acylating, alkylating or sulfonylating agent.

* * * * *